United States Patent
Skrædderdal et al.

(10) Patent No.: US 10,925,289 B2
(45) Date of Patent: Feb. 23, 2021

(54) METHOD AND SYSTEM FOR BATCHING SIZE ADJUSTED FOOD ITEMS

(71) Applicant: MAREL A/S, Aarhus N (DK)

(72) Inventors: Henning Skrædderdal, Viby J (DK); Henrik Kristiansen, Ronde (DK)

(73) Assignee: MAREL A/S, Aarhus N (DK)

( * ) Notice: Subject to any disclaimer, the term of this patent is extended or adjusted under 35 U.S.C. 154(b) by 163 days.

(21) Appl. No.: 16/070,937

(22) PCT Filed: Jan. 18, 2017

(86) PCT No.: PCT/EP2017/050973
§ 371 (c)(1),
(2) Date: Jul. 18, 2018

(87) PCT Pub. No.: WO2017/125431
PCT Pub. Date: Jul. 27, 2017

(65) Prior Publication Data
US 2019/0029277 A1    Jan. 31, 2019

(30) Foreign Application Priority Data
Jan. 18, 2016 (EP) .................................. 16151731

(51) Int. Cl.
*G01G 15/02*    (2006.01)
*G01G 15/04*    (2006.01)
(Continued)

(52) U.S. Cl.
CPC .............. *A22C 17/002* (2013.01); *B07C 5/38* (2013.01); *B26D 7/32* (2013.01); *G01N 33/12* (2013.01)

(58) Field of Classification Search
CPC .......... A22C 17/002; B07C 5/38; B26D 7/32; G01N 33/12; G01G 15/02;
(Continued)

(56) References Cited

U.S. PATENT DOCUMENTS 4,313,507 A * 2/1982 Hays .................... G01G 19/393
                                                              177/1
4,336,853 A * 6/1982 Hirano .................. G01G 19/343
                                                              177/25.18
(Continued)

FOREIGN PATENT DOCUMENTS

CN    201930933 U    8/2011
CN    103157607 A    6/2013
(Continued)

OTHER PUBLICATIONS

Chinese Office Action from CN Application No. 201780006928.2, dated Mar. 4, 2020.
(Continued)

*Primary Examiner* — Randy W Gibson
(74) *Attorney, Agent, or Firm* — Workman Nydegger

(57) ABSTRACT

A method for processing and batching food items in a food processing system according to a predefined batch target criterion, comprises the steps of conveying a food item to weight determining means, determining the weight of the food item by means of the weight determining means, and processing the determined weight of the food item together with a weight of a plurality of food items. The processing includes dynamically generating a control-cutting signal. The method further comprises determining if the dynamically generated control cutting signal indicates that cutting off a part of the food item will increase a prospect to meet the predefined batch target criterion, and in the confirmative convey the food item to a separation device wherein a part of the food item is cut off.

24 Claims, 3 Drawing Sheets

(51) Int. Cl.
*G01G 19/387* (2006.01)
*G01N 33/12* (2006.01)
*A22C 17/00* (2006.01)
*B07C 5/38* (2006.01)
*B26D 7/32* (2006.01)

(58) Field of Classification Search
CPC ....... G01G 2015/022; G01G 2015/025; G01G 2015/027; G01G 15/04; G01G 2015/042; G01G 2015/045; G01G 2015/047; G01G 19/30; G01G 19/387; G01G 19/393
See application file for complete search history.

(56) References Cited

U.S. PATENT DOCUMENTS

| | | | | |
|---|---|---|---|---|
| 4,794,996 A * | 1/1989 | Wallace | ............... | B26D 7/30 |
| | | | | 177/1 |
| 5,668,634 A * | 9/1997 | Newman | ............... | A22B 5/007 |
| | | | | 348/89 |
| 7,775,373 B2 * | 8/2010 | Grundtvig | ............... | B65B 5/105 |
| | | | | 209/542 |
| 8,759,694 B2 * | 6/2014 | Weber | ............... | G01G 13/04 |
| | | | | 177/119 |
| 8,862,262 B2 * | 10/2014 | Thorsson | ............... | A22C 17/0093 |
| | | | | 700/213 |
| 8,869,990 B2 * | 10/2014 | Skyum | ............... | B07C 5/3422 |
| | | | | 209/645 |
| 9,919,445 B2 * | 3/2018 | Mikkelsen | ............... | B26D 7/0625 |
| 2010/0051513 A1 | 3/2010 | Skyum et al. | | |
| 2012/0128838 A1 | 5/2012 | Virippil et al. | | |

FOREIGN PATENT DOCUMENTS

| | | |
|---|---|---|
| CN | 103875790 A | 6/2014 |
| CN | 204470140 U | 7/2015 |
| CN | 104822271 A | 8/2015 |
| EP | 2268149 A2 | 1/2011 |
| EP | 2745942 A1 | 6/2014 |
| EP | 3045882 A1 | 7/2016 |
| WO | 2014083148 A1 | 6/2014 |
| WO | 2014169925 A1 | 10/2014 |

OTHER PUBLICATIONS

Extended European Search Report from EP Application No. EP 16151731.3, dated Nov. 8, 2016.
International Search Report from PCT Application No. PCT/EP2017/050973, dated Mar. 28, 2017.

* cited by examiner

METHOD AND SYSTEM FOR BATCHING SIZE ADJUSTED FOOD ITEMS

FIELD OF THE INVENTION

The invention relates to processing of food items, such as meat items, vegetables, fruit, etc. Particularly the invention relates to method for adjusting size of food items to meet batching requirements.

BACKGROUND

Batching food items such as pieces of meat, e.g. chicken fillets into fixed weight trays, may need to be performed so that the weight of each batch meets a certain weight criterion, e.g. so that each batch meets a certain minimum and/or maximum weight.

The weight criteria may need to be met by selecting a fixed or variable number of food items for a given batch. In some batching processes, one or more of the selected food items may be adjusted in size, e.g. by cutting the food item, in order to better meet the weight criterion.

Since the weight of such food items may vary in weight it is a problem to cut the food items so that the weight criteria are addressed in an effective way in view of the processing method.

From U.S. 2010/051513 A1 it is known to reduce the weight of a food item in a food processing system before the food item is batched, if the weight of the food item exceeds a predefined target value. However, this can cause excess weight trimming or undesired overweight of the batches.

Therefore, it is an object of the invention to provide methods for adjusting the size or weight of food items so that batching can be performed more effectively, e.g. so that overweight of batches can be reduced.

BRIEF DESCRIPTION OF THE INVENTION

An aspect of the invention relates to a method for processing and batching food items in a food processing system, where said batching of food items is performed according to at least one predefined batch target criterion, said method comprising the steps of:
conveying a food item to weight determining means,
determining the weight of said food item by means of said weight determining means,
processing said determined weight of said food item together with a weight of a plurality of food items in said food processing system, wherein the processing includes dynamically generating a control cutting signal,
if said dynamically generated control cutting signal indicates that cutting off a part of said food item will increase a prospect to meet the at least one predefined batch target criterion, then convey said food item to a separation device wherein a part of said food item is cut off where after said food item is conveyed to a food item batching system, and transporting said food item to a food item batch in response to said at least one predefined batch target criterion.

The control cutting signal may be any signal such as a logical signal which indicates that cutting said food item, e.g. a food item approaching the separation device, may advantageously be cut in order to increase a prospect to meet the at least one predefined batch target criterion. Accordingly, based on a food item which has been cut, this cut food item together with one or more of the plurality of food items in said food processing system may increase a prospect to meet the at least one predefined batch target criterion. Cutting said food item may increase a prospect to meet the at least one predefined batch target criterion, e.g. in terms of a prospect to meet a predefined batch target weight for one or more food item batches about to be completed on basis of one or more of the plurality of food items together with said food item.

Advantageously, the decision to cut said food item is performed in response to the control cutting signal, where the control cutting signal is generated dynamically based on said determined weight of said food item together with a weight of a plurality of food items in said food processing system. Accordingly, the decision to cut said food item is performed dynamically dependent on weights of said food item and the plurality of food items. Therefore, the decision to cut said food item dynamically takes into account natural variations in e.g. weights of the incoming food items entering the food processing system. Particularly, the decision to cut said food item dynamically takes into account natural weight variations of the plurality of food items already present in the food processing system together with said food item under consideration for being weight reduced, i.e. takes into account variations in the weight distribution of the plurality of food items together with said food item.

Therefore, advantageously, the decision to cut a food item is not based on static assumptions but takes into account variations in size, shape, weight and/or other conditions of the food items, particularly of a plurality of food items together with said food item.

Said at least one predefined batch target criterion may comprise or may be a predefined target value, such as a weight target or predefined batch target weight. For example, the predefined batch target criterion may be a predefined weight target relating to a target weight of the food item batches, e.g. a target weight of a finished batch or a predefined item target weight of individual food items to be accommodated in a batch containing a certain number of food items (N-item batch).

Alternatively or additionally, the at least one predefined batch target criterion may comprise or relate to a maximum average overweight of the food item batches, a weight range e.g. a target weight with positive and negative tolerances and/or a number of food items to be accommodated by the food item batches.

It should be noted that the term "weight determining means" in this context should be interpreted as any kind of weighing device suited for determining the weight of the food items, i.e. any kind of vision based, camera based, X-ray based, laser-scanning based, or ultrasound based weighing device, or other or combinations thereof. Alternatively, any kind of displacement weighing devices, e.g. strain-gain based weighing devices or any other force based weighing devices may be used.

It should also be noted that the term "batching system" in this context should be interpreted as any kind of system arranged to group food items according to predefined criterions according to e.g. number of food items in each batch, total weight of batch, color and/or shape of food items in each batch and/or other.

After transporting (moving) said food item to a food item batch, said food item batch may be transported out of said food processing system, e.g. when it is completed.

An aspect of the invention further comprises a step of determining if said dynamically generated control cutting signal indicates that cutting off a part of said food item will not increase said prospect to meet the at least one predefined batch target criterion, if so, then convey said food item to said food item batching system without cutting off any part of said food item.

An aspect of the invention comprises determining an average weight of a plurality of food items in said food processing system, and dynamically generating the control cutting signal and use to reduce the weight of said food item, if reducing the weight of said food item will bring said average weight closer to an ideal average weight of said food item according to the predefined batch target criterion, such as a predefined target value, target weight or batch target weight.

The plurality of food items may include a selection of said plurality of food items and may include said food item, i.e. a selected plurality of food items. Accordingly, based on a plurality of the food items the control cutting signal is dynamically generated and used to reduce the weight of said food item, if reducing the weight of said food item will bring an average weight of a plurality of food items in said food processing system closer to an ideal average weight of the food item according to the predefined target value. Alternatively, the control cutting signal is dynamically generated and used to reduce the weight of said food item, if reducing the weight of said food item will increase a prospect to meet the at least one predefined batch target criterion.

The plurality of food items (i.e. the selected plurality of food items) including a selection of said plurality of food items and possibly including said food item may be determined as a number or selection of the heaviest food items comprised by said food item and said plurality of food items.

Advantageously, when the average weight of the plurality of food items is brought closer to an ideal average weight of the food items according to the predefined target value, the average overweight of the food item batches may be reduced. The overweight reduction is performed dynamically and may therefore continuously minimize the average overweight.

An aspect of the invention comprises comparing said determined weight of said food item with an average weight of a plurality of food items in said food processing system and dynamically generating a control cutting signal and use to reduce the weight of said food item, if reducing the weight of said food item will bring said average weight closer to an ideal average weight of said food item according to said predefined batching criteria.

In an aspect the batching criteria is constituted by the predefined batch target criterion.

The comparison may involve a process which determines if cutting said food item will bring said average weight closer to the predefined target value, e.g. a process where the average weight of said food item together with a plurality of the food items, e.g. a plurality of food items located downstream of the separation device, is determined.

An aspect of the invention comprises determining an amount to be cut off from said food item based on comparing the determined average weight with the predefined target value. Accordingly, amounts to be cut from said food item may be determined dynamically dependent on natural variations in weights of the incoming food items.

For example, the amount to be cut from said food item may be determined as the total weight of the selection of food items minus the batch target weight multiplied by number items in the selection of food items divided by the number of items in each batch.

An aspect of the invention comprises batching said food item in a food item batch in response to one or more predefined batching criteria.

In an aspect of the invention said one or more predefined batching criteria comprise a number target regarding the number of food items in each food item batch.

In a further aspect of the invention said one or more predefined batching criteria comprise an appearance target regarding the appearances of the food items in each food item batch.

In a further aspect of the invention said one or more predefined batching criteria comprise two or more different weight targets.

In an aspect of the invention said average weight is determined on the basis of the weight of the last four food items in said food processing system, preferably the last eight food items in said food processing system and most preferred the last twelve food items in said food processing system.

If the average weight is determined on the basis of too few food items the risk of excess cutting or batch overweight is increased. However, if the average weight is determined on the basis of too many food items the information can become too difficult or too complex to handle which could reduce the capacity of the food processing system. Thus, these numbers of food items present an advantageous relationship between efficiency and capacity.

The at last four, at least eight or at least twelve food items in said food processing system may be constituted by food items from A) at least some of the food items that are ready to be moved to batches, B) at least some of the items that have been moved to batches and/or C) said food item under consideration for being reduced in size.

In an aspect of the invention, said plurality of food items include of at least some of the food items in the food item batches in said food processing system.

Basing the cutting decision on the weight of at least some of the food items in the food item batches in the food processing system is advantageous in that this will increase the chance of bringing the weight of the batches closer to the desired weight target.

In an aspect of the invention said plurality of food items includes of at least some of the food items having passed said separation device but have not already been batched.

Basing the cutting decision on the weight of at least some of the food items having passed said separation device is advantageous in that this will further increase the chance of bringing the weight of the batches closer to the desired weight target.

In an aspect of the invention said plurality of food items includes of at least one food item having passed said weight determining means but have not passed said separation device. This at least one food item is also referred to as the food item under consideration.

Including the food item under consideration in the plurality of food items will reduce the risk of excessive weight reduction.

In an aspect of the invention said predefined target value is at least one weight interval. Alternatively or additionally, the said predefined target value may comprise or be weight target or predefined batch target weight such as a weight target relating to a target weight of the food item batches. Thus, in general the predefined target value may comprise a value related to target weight of the batches.

In an aspect of the invention said control cutting signal is only executed if the weight of said food item can be advantageously reduced by more than a predefined minimum cut-off weight.

In an aspect of the invention the step of processing said determined weight of said food item together with a weight of the plurality of food items in said food processing system comprises determining in descending order of weights of the plurality of food items a selection of at least one of the plurality of food items so that the selection of food items has an average weight which meets the predefined batch target criterion.

For example, the selection of at least one of the plurality of food items may be performed by determining the total weight of the selection of food items minus the batch target weight multiplied by number items in the selection of food items divided by the number of items in each batch. Or selection of at least one of the plurality of food items may be performed by determining the heaviest food items of the plurality of food items together with said food item, which together on average weigh more than the predefined batch target weight divided by the number of items in the batch.

In an aspect of the invention the step of determining if the dynamically generated control cutting signal indicates that cutting off a part of said food item will increase a prospect to meet the at least one predefined batch target criterion, comprises determining an amount to be cut from said food item, if said food item is included in the selection of food items.

Determining an increase of the prospect to meet the at least one predefined batch target criterion may involve determining if the total weight of the selection of food items is greater than the predefined batch target weight multiplied by the number of food items in the selection of food items divided by the number of items in each batch.

Determining an amount to be cut from said food item may be determined as the total weight of the selection of food items minus the batch target weight multiplied by number items in the selection of food items divided by the number of items in each batch.

An aspect of the invention further comprises determining, if said food item is not included in the selection of food items, determining a total weight of the remaining food items of the plurality of food items which is not included in the selection of food items, and determining an amount to be cut from said food item based on the total weight of the remaining food items and the predefined batch target weight.

An aspect of the invention relates to a food processing system for processing and batching food items, said processing system comprises
conveyor means for conveying said food items through at least parts of said food processing system,
weight determining means for determining the weight of said food items,
a batching system arranged to batch said food items according to one or more predefined batching criteria,
a separation device positioned downstream in relation to the weight determining means and upstream in relation to the batching system, arranged to cut off a piece of said food items in accordance with a control cutting signal, and
a control system for controlling the batching system and the food item separation device,
wherein said control system is arranged for dynamically generating said control cutting signal on the basis of information regarding the determined weight of more than one food item in said food processing system.

By arranging the control system so that the decision regarding if a particular food item should be reduced in weight is take on the basis of the weight of several food items in the food processing system—and not just on the basis of a predetermined weight limit—it is possible to make a more correct decision compared to what is possible with the prior art systems—thus reducing the risk of excess weight reduction and/or batch overweight.

It should be noted that the term "conveyor means" in this context should be interpreted as any kind of conveyor suited for transporting or conveying the food items, i.e. any kind of belt conveyors, chain conveyors, roller conveyors, or other or combinations thereof.

In an aspect of the invention the weight determining means further comprises shape determining means for determining a shape and a position of said food item.

It should be noted that the term "shape determining means" in this context should be interpreted as any kind of shape determining device, suited for determining the shape of the food items, i.e. any kind of vision based, camera based, laser line based, or ultrasound based shape determining device, or other or combinations thereof.

In an aspect of the invention, said separation device is adapted for cutting off said piece of said food item in response to input from said shape determining means.

Accordingly, the shape determining means may provide information relating to the shape and position of said food item enabling said separation device to cut off a desired part of the food item in a suitable way.

In an aspect of the invention, the food processing system comprises further weight determining means positioned downstream in relation to said separation device and upstream in relation to said batching system.

The further weight determining means may be of the same type as the previously discussed weight determining means, e.g. a vision based, camera based, laser-scanning based, or ultrasound based weighing device, or other or combinations thereof. Alternatively, any kind of displacement weighing devices, e.g. strain-gain based weighing devices may be used for the further weight determining means.

In an aspect of the invention said food processing system further comprises a rejecter device positioned downstream in relation to said separation device for automatically rejecting cut-off material of said food item.

In an aspect of the invention said food processing system comprises cut-off checking means arranged for checking if cut-off material has been properly removed from said food item.

It should be noted that the term "cut-off checking means" in this context should be interpreted as any kind of cut-off checking device suited for checking if the cut-off material has been properly removed from said food item, i.e. any kind of vision based, camera based, laser-scanning based, or ultrasound based checking device, or other or combinations thereof. It may also be implemented by using the "further weight determining means" and compare the found weight with the expected weight.

In an aspect of the invention, the control system is arranged to not batch a specific food item if said cut-off checking means detect that cut-off material has not been properly removed from said specific food item.

In an aspect of the invention said basis of said information regarding the determined weight of said more than one food item includes at least one food item approaching said separation device and at least some of the food items having passed said separation device.

In an aspect of the invention said control system is arranged for using said information regarding said determined weight of said more than one food item to establish an average weight of said more than one food item and compare said determined weight of said food item with said average weight.

In an aspect of the invention said control system is arranged for using said information regarding said determined weight of said more than one food item to establish an average weight of said more than one food item and compare said average weight with a weight relating to the predefined batch target criterion.

For example, the control system may be arranged to establish an average weight of a selection of said plurality of food items and possibly including said food item (food item under consideration) to establish an average weight of the selection of food items and to compare the average weight with a target weight determined as the predefined batch target weight divided by the number of food items the batch.

An aspect of the invention relates to a food processing system according embodiments of the invention, wherein said food processing system is arranged to perform said method according to embodiments of the invention.

BRIEF DESCRIPTION OF THE DRAWINGS

The invention will be described in the following with reference to the figures in which.

DESCRIPTION OF THE INVENTION

Figure 1:
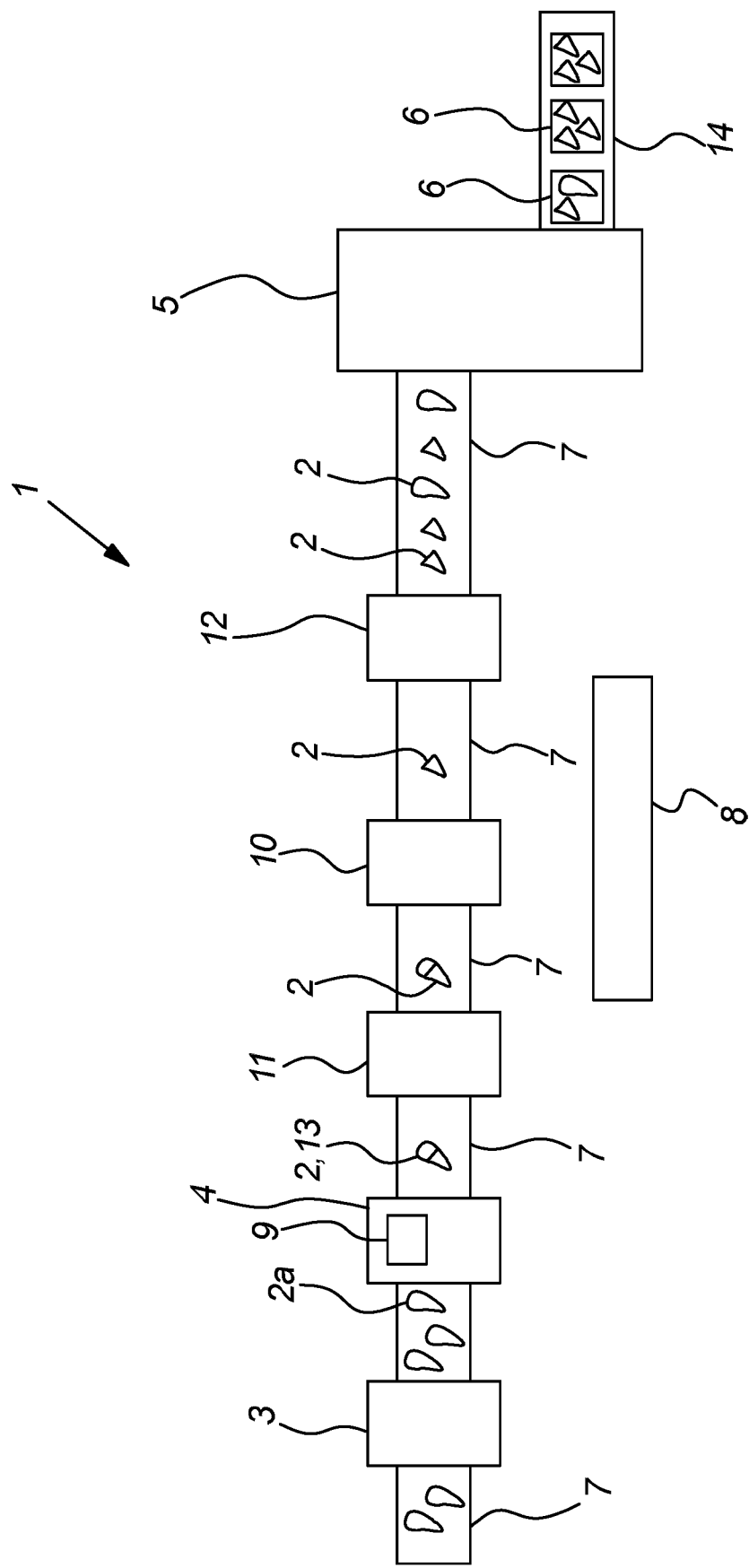
FIG. 1 shows a food processing system.

FIG. 1 shows a food processing system 1 for processing and batching food items 2, 2a. The processing system 1 comprises conveyor means 7 for conveying said food items through at least parts of said food processing system 1. The processing system 1 further comprises weight determining means 3 for determining the weight of said food items 2, a separation device 4 arranged to cut off a piece of said food item in accordance with a control cutting signal, a batching system 5 arranged to batch said food items according to one or more predefined batching criteria.

The batching system 5 may comprise at least one controllable handling means 15 (see FIG. 2) capable of transferring food items 2 from the conveyor means 7 to batches 6 on a batch conveyor 14.

The weight determining means 3 is arranged at the conveyor means 7 for determining the weight of said incoming food items 2, the separation device 4 is positioned downstream in relation to the weight determining means 3 and upstream in relation to the batching system 5.

The food processing system 1 further comprises a control system 8 for controlling the batching system 5 and the food item separation device 4. The control system 8 may receive input, e.g. determined weight information from the weight determining means 3, batching information from the batch system 5 relating to food items 2 having been batched or not.

The control system 8 is arranged for dynamically generating said control cutting signal on the basis of information regarding the determined weight of more than one of the food items in said food processing system 1.

The basis of the information regarding the determined weight of the more than one food items may include at least one food item 2a approaching the separation device 4 and at least some of the food items 2 having passed said separation device 4, i.e. food items located downstream of the separation device 4.

Since the control cutting signal is generated dynamically, the control cutting signal may be determined adaptively, e.g. so that the separation device is dynamically controlled to cut off a piece of said food item 2a, where the piece to be cut off is determined dependent on the information regarding the determined weight of more than one food item in said food processing system.

Thus, the decision regarding if the food item 2a under consideration advantageously can be reduced in size is taken on the basis of the weight of several food items already present in the system 1, including the food item 2a under consideration, so that the decision criteria—i.e. the criteria for determining a possible increase in the prospect to meet the at least one predefined batch target criterion—changes dynamically in response to the current supply of food items and the actually predefined batch target criterion.

The separation device 4 may be embodied by cutting means, e.g. a sword-type knife suspended in a rotatable manner with its suspension point at the side of a gap in the conveyor 7, e.g. a gap between two conveyors that are installed end to end. If a piece of an item is decided to be cut off, the knife is rotated through the gap when the position determined for cutting the item, is in line with the gap. The cut can be performed vertically from above or it can be performed with an angle in which case the item will appear more natural than if it is cut vertically from above.

In another embodiment the separation device 4 may also or instead comprise a rotating disc cutter, a laser cutter, a water jet cutter or other.

The separation device 4 could be arranged to cut the food item in a straight line but is could also be arranged to cut the food item along a more complex curvature e.g. to ensure that the cut food item still would resemble a complete food item. Or the separation device 4 could also or instead be arranged to cut the food item so that both parts of the separated food item could be used in food item batches—i.e. in such an embodiment the cut-off part would also be batched.

The food processing system 1 may further comprises shape determining means 9 for determining a shape and a position of said food item. According to an embodiment, the shape determining means 9 is comprised by the separation device 4. The separation device 4 may be adapted for cutting off a piece of said food item 2a in response to input from said shape determining means 9. The weight determining means 3 and the shape determining means 9 may be combined in one means, i.e. the shape is determined and from the shape the volume and the weight is calculated or estimated. This will be discussed in more details later.

The food processing system may further comprise a further weight determining means 10 positioned downstream in relation to said separation device 4 and upstream in relation to said batching system 5.

The food processing system may further comprise a rejecter device 11 device positioned downstream in relation to said separation device 4 for automatically rejecting cut-off material of said food item. The rejecter device 11 may be located upstream relative to the further weight determining means 10.

The rejecter device 11 may comprise an air pressure rejecter, a controllable gap between conveyers, a robot, an ejector arm or other devices suited for rejecting food items and/or any combination thereof.

Additionally, the food processing system 1 may comprise a cut-off checking means 12 arranged for checking if cut-off material has been properly removed from said food item. For example, the control system 8 may be arranged to not batch a specific food item if said cut-off checking means 12 detects that cut-off material has not been properly removed from said specific food item. The cut-off checking means 12 can be a weight determining device that compares the the weight of the items after it has passed the separation device 4 and the rejector device 11 with the weight of the same items when its weight was determined at the weighing determining means 3, taken in consideration how much should be cut off. Further this weight determining device can partly be identical to the further weight determining means 10.

There can be set limits for how much and how little that it is allowed to cut off in the food item separation device 4. A minimum limit can be set to avoid that a cut off part cannot be controlled simply because it is too small, and a maximum limit can be set to avoid that the main piece is too odd shaped compared to its natural shape. These limits can be set in gram or millimeters (number or percentage).

In an embodiment, the food processing system 1 comprises a tracking system configured to track every food item 2 through the process in the food processing system 1. The batching system 5 may use the tracking information for correctly selecting the food items to be batched.

As an example for determining the control cutting signal, e.g. on the basis of the determined weight of at least one food item 2a approaching the separation device and at least some of the food items having passed said separation device, the control cutting signal may be determined on basis of
A) the weight of the items 2 that are ready to be moved to batches 6 (i.e. food items 2 located between the output of the separation device 4 and the input of the batching system 5, or at least some of them,
B) the weight of at least some of the items that have been moved to batches 6 and/or which have left the input to the batching system and
C) the weight of the item 2a under consideration for being reduced in size.
Thus, on basis of the information regarding the determined weight of more than one of the food items 2, 2a in the food processing system it is decided if the item under consideration advantageously can be reduced in size. This will be discussed in more details later.

To recap the concept and clarify some details:

The food processing system may be configured to perform batching of food items according to at least one predefined batch target criterion. The batching includes conveying a food item 2 to the weight determining means 3 in order to determine the weight of said food item 2. The batching further includes processing said determined weight of said food item 2 together with a weight of a plurality of food items 2 in said food processing system and dynamically generating a control cutting signal.

With reference to FIG. 1, the processing may include processing the determined weight of the food item 2a approaching the separation device together with weights of a plurality of food items. The plurality of food items may include the items referred to under A) and B) above. The food item 2a approaching the separation device is equally referred to as the food item 2a under consideration.

On basis of the control cutting signal determined dynamically dependent on the weights of the plurality of food items 2, 2a, then—if the dynamically generated control cutting signal indicates that cutting off a part of the food item 2a under consideration will increase a prospect to meet the at least one predefined batch target criterion, then the cutting device 4 is instructed cut off a part of said food item 2a in a separation device. After the food item 2a has been cut, the separated food item or a separated part of the food item is conveyed towards the food item batching system 5.

Further, on basis of the control cutting signal, then—if the dynamically generated control cutting signal indicates that cutting off a part of food item 2a under consideration will not increase said prospect to meet the at least one predefined batch target criterion then said food item 2a is conveyed towards said food item batching system without cutting off any part of said food item.

After the food item 2a under consideration has been conveyed to the batching system 5, the food item is conveyed (i.e. moved) to a food item batch 6 and thereafter—when the bath is completed said food item batch 6 is conveyed out of said food processing system.

Some more about how to generate the control cutting signal:

The predefined batch target criteria may be a predefined weight target (or weight target+/−tolerances) relating to weights of the batches 6.

Accordingly, in the context of increasing the prospect to meet the at least one predefined batch target criterion, the dynamically generated control cutting signal may indicate that cutting off a part of the food item under consideration will improve how the plurality of food items 2, including the food item 2a under consideration, meets the predefined batch target criteria.

In the example described below, it is described how the control cutting signal and a size to be cut is determined based on the weights of 4 food items 2 that are ready to be moved to batches 6, the weights of 20 food items 2 that have already been moved to batches 6 (but unfinished batches), and the weight of a single food item 2a under consideration for being reduced in size. Accordingly, the plurality of food items 2, 2a is in this example constituted by 25 food items.

The size to be cut from a food item 2a may be in terms of a weight, a volume, a length or other measures relating to a size of the food item.

In this example, the target criterion for a batch is 400 g consisting of two or three food items. To avoid underweight, the target criteria regarding the batch weight is set slightly above the 400 g batch weight, e.g. to a predefined batch target criterion in the interval from 401 g to 404 g, here a predefined batch target criterion of 404 g.

To decide whether or not to cut the food item 2a under consideration, the 25 food items 2 are put in sequence by weight (or estimated weight). It can then be decided how many of these food items 2 that qualify for being used in batches 6 with only two items. I.e. if e.g. the 10 heaviest food items 2 together on average weigh more than 202 g (decision target 404 g divided by 2 items) then these food items 2 qualify for that. If e.g. the total weight for these ten food items 2 is 2030 g and the food item 2a under consideration is among these ten items 2, then it will be decided that this food item 2a shall be reduced in size with 10 g such that the average of the largest ten food items is 202 g. However, if the food item 2a under consideration is not among the ten largest items, then the sum of the remaining fifteen food items 2 is found—which could be e.g. 2090 g. Fifteen food items 2 distributed with three in each batch 6 will form five batches 6. Five batches 6 with 404 g in each make a total of 2020 g. Hence, the food item 2a under consideration will in this embodiment have to be reduced in size with 70 g (2090 g minus 2020 g) such that the sum of the fifteen smallest food items 2 is reduced to a total weight of 2020 g.

Thus, the general process according to this example is that the food-item weights are sorted in a list with highest weights first. An algorithm then considers—or we can call it "removes" food items 2 from start of the list until the removed food items have an optimal average weight for the lowest item count (e.g. 2-item batches) or the list is empty. Accordingly, food items may be removed from the sorted list until the average weight of the removed food items meets the ideal average weight of the food item according to the predefined batch target criterion. For example, food items 2 may be removed from the list until the average weight of the food items 2 is at most a threshold weight (e.g. 2 g) larger than the ideal average weight of said food item according to the predefined batch target criterion, or until inclusion of the next food item will generate an average weight which is lower than the ideal average weight of said food item according to the predefined batch target criterion. If, after removal of the food items 2, the list is empty, the excess weight is the difference between the actual average weight and the target average weight, i.e. the ideal average weight of said food item according to the predefined batch target criterion where the difference is multiplied with number of food items removed from the list. If the list is not empty, a similar process is performed on the next lowest item count (e.g. 3-item batches) and so on, until the list is empty or higher item count is not allowed. If the list becomes empty this means overweight, i.e. the average weight is greater than the predefined batch target criterion.

Another example: If the predefined batch target weight criterion of each batch is 900 gram and the number of food items in each batch is predefined as three items, then the ideal average weight of each food item according to the predefined batch target criterion would be 300 gram. Likewise, if the predefined batch target weight criterion of each batch is 500 gram and the number of food items in each batch is two items, then the ideal average weight of the food item according to the predefined batch target criterion would be 250 gram.

Accordingly, the control system 8 may be arranged for using information regarding the determined weight of said plurality of food items 2 together with the food item 2a under consideration to establish an average weight of these food items and to compare this established average weight with a target average weight, e.g. the predefined batch target criterion. As described above, based on the comparison, it is possible to determine the excess weight and, therefore, if the food item should be cut, possibly the amount (e.g. weight) to be cut, or if the food item should not be cut, e.g. if the excess weight is lower than a cutting threshold weight.

Accordingly, an embodiment relates to determining an amount to be cut off from the food item 2a based on comparing the determined average weight with a predefined target value, e.g. target average weight.

In another embodiment, the control system 8 may be arranged for using information regarding the determined weight of the plurality of food items 2 together with the food item 2a under consideration to establish an average weight of said food items and to compare the determined weight of the food item 2a under consideration with this established average weight.

According to an embodiment, when food items 2 are removed from the list, i.e. removed for placing in a batch 6, this can be done in fractions of a weight of a food item 2 to obtain optimal average weight before going on with the next higher item count. The fraction of the food item can be obtained for unprocessed food items by determining the control cutting signal for the separation device 4 to cut an unprocessed food item to obtain the desired fraction of a food item.

A reasonable number of food items 2 to be used as the number of food items already batched (in the above example it is 20 items) can be found as a fraction (F) of the total number of food items 2 that can be in the batches 6 currently being filled. If e.g. sixteen batches 6 are under filling simultaneously in the batching system 5 with two or three food items 2, i.e. on average 2.5 items in each batch, sixteen times 2.5=40 food items 2 can be said to be in the batches 6 that are under filling (when they are finished). The fraction (F) can be chosen to be 0.5. Hence, a reasonable number to be used as the number of food items 2 already batched would then be twenty. The factor F can be adjusted up and down depending on the raw material, if e.g. the determined weights of the incoming food items 2 often changes in size, then a smaller factor than 0.5 can be used, and opposite, if the determined weights of the incoming food items 2 is very constant in size, then a factor higher than 0.5 can be used.

According to another embodiment on how to generate the control cutting signal: The previously accepted food items in the previously accepted food item history (i.e. not including the food item 2a under consideration) are sorted into groups of N-item batches. The sorting into groups is performed dependent on at least one predefined batch target criterion, e.g. a predefined batch target weight. For example, each N-item group may have a predefined batch target criterion, e.g. a predefined batch target weight or a predefined item target weight. E.g. an N-item group may have an optimal or target average weight given as the "predefined batch target weight" divided by N=T/N For example, the predefined batch target weight, e.g. 540 g, is divided with the possible different numbers of food items 2 in batches 6 and hence a group for each items-per-batch is defined. This gives the following optimal predefined item target weights for the N-item batches:

Predefined item target weight for 2-item batches: 540 g/2 items=270 g

Predefined item target weight for 3-item batches: 540 g/3 items=180 g

Accordingly, either the predefined batch target weight (540 g or slightly higher) or predefined item target weights (270 g and 180 g) may be used.

Sorting may be performed dependent on food item weight limits which for an N-item group may be defined dependent on the predefined item target weight of neighbor N-item groups.

For example, the sorting could be performed based on the mid-point weight between the N-item groups:

Mid-point between group 1 and group 2: (270+180)/2 [g]=225 g

Hence, the plurality of food items 2 are split up between the groups at the mid-point so that the food items with a weight above 225 g belongs to the 2-item group, and the food items with a weight from zero and up to 225 g belongs to the 3-item group.

Based on a food item 2a under consideration, the N-item group which provides the best possible match with the food item 2a under consideration—with or without cutting for the food item 2a under consideration—is determined. The best possible match is searched from the N-item group having the lowest number N and up to the group with the highest number N. The best possible match may be determined from different criteria, e.g. the lowest amount to be cut off In a next step the average weight of the items in the groups is found. For example, food items in the 2-item group may have an average weight of 270 g and food items in the 3-item group may have an average weight of 220 g.

If the food item 2a under consideration has a weight above the mid-point weight, i.e. if it belongs to the 2-item group, it is firstly investigated if it will do any good in the 2-item group. In this example, the food item 2a under consideration weighs 260 g.

In this case it will lower the 2-item group average weight by some grams. If it is allowed to lower the average below the optimum group item average (i.e. the predefined item target weight), the search is continued by investigating how it will influence the next group (i.e. the 3-item group). Finally it will be considered where it contributes best to the overall performance and that will be the final result of the investigation and will be carried out.

In this example the actual 3-item group average weight (220 g) is already higher that the optimum average weight (180 g), so the final result of the investigation of the 3-item group will result in that the average weight of the 3-item group will increase further. Hence, most probably, if it is allowed to lower the actual group item average below the optimum group item average (predefined item target weight) of the 2-item group, then the food item $2a$ under consideration will be chosen to go to the 2-item group without cutting anything off the item $2a$ under consideration. On the other hand, if it is not allowed to lower the actual group item average below the predefined item target weight of the 2-item group, then the item will be chosen to go the 3-item group.

Accordingly, in this example, the determined weight of the food item $2a$ under consideration is processed together with a weight of a plurality of food items 2 in said food processing system belonging to one of the N-item groups and control cutting signal is dynamically generated to determine if cutting off a part of the food item $2a$ under consideration will increase a prospect to meet the at least one predefined batch target criterion. In this example, the predefined batch target criterion comprises at least one of the predefined item target weights, which is compared with the average weight of the food item $2a$ under consideration together with a plurality of food items in one of the N-items groups for determining how the food item $2a$ under consideration should be processed.

As already mentioned the food item $2a$ under consideration will increase the actual item average weight of the 3-item group, and hence the food item $2a$ will be subject to cutting. There may be limitations to how much that is allowed to be cut off. For example, a cut limit may set to 25% of the item weight. Here 260 g times 0.25=65 g. Hence it is chosen to cut off 65 g of the item $2a$ under consideration such that after cutting it will weigh 195 g and such that the average weight of the 3-item group will be reduced and come closer to the optimal average weight (predefined item target weight) of the 3-item group (from 220 g towards 180 g).

According to even another embodiment, the predefined batch target weight is divided with the different numbers of food items of relevant batches 6. If the predefined batch target weight target weight is 540 g, and batches 6 to be completed contains 3 or 4 food items per bath, the following optimal predefined item target weights for the N-item batches are determined:

Predefined item target weight for 3-item batches: 540 g/3 items=180 g

Predefined item target weight for 4-item batches: 540 g/4 items=135 g

The plurality of food items 2 in the food processing system and the food item $2a$ under consideration are sorted in descending order of weights of the food items.

First it is found how many food items that can be used with 3 food items per batch, beginning with the heaviest food items. Thereafter the method is continued with 4 items per batch and so on. Table 1 illustrates the result of the first part of the method:

TABLE 1

| Item weight [g] | Excess weight to 180 g | Accumulated excess weight [g] | Number of items |
|---|---|---|---|
| 191 | 11 | 11 | 1 |
| 188 | 8 | 19 | 2 |
| 185 | 5 | 24 | 3 |
| 182 | 2 | 26 | 4 |
| 179 | −1 | 25 | 5 |
| 176 | −4 | 21 | 6 |
| 173 | −7 | 14 | 7 |
| 170 | −10 | 4 | 8 |
| 167 | −13 | −9 | 9 |

Table 1 shows that 8 food items can be used plus a fraction of 4 g since the accumulated excess weight is 4 g.

The method is continued with a second part of the method, now with the excess weight transferred from the eighth food item:

TABLE 2

| Item weight [g] | Excess to 135 g | Accumulated excess weight [g] | Number of items |
|---|---|---|---|
|  |  | 4 |  |
| 167 | 32 | 36 | 9 |
| 167 | 32 | 68 | 10 |
| 164 | 29 | 97 | 11 |
| 161 | 26 | 123 | 12 |
| 158 | 23 | 146 | 13 |
| 155 | 20 | 166 | 14 |
| 152 | 17 | 183 | 15 |
| 149 | 14 | 197 | 16 |
| 146 | 11 | 208 | 17 |
| 143 | 8 | 216 | 18 |
| 140 | 5 | 221 | 19 |
| 137 | 2 | 223 | 20 |
| 134 | −1 | 222 | 21 |
| 131 | −4 | 218 | 22 |
| 128 | −7 | 211 | 23 |
| 125 | −10 | 201 | 24 |
| 122 | −13 | 188 | 25 |
| 119 | −16 | 172 | 26 |
| 116 | −19 | 153 | 27 |
| 113 | −22 | 131 | 28 |
| 110 | −25 | 106 | 29 |
| 107 | −28 | 78 | 30 |

In this case the list of food items is empty after 30 items and the accumulated excess weight is 78 g.

Now the food item $2a$ under consideration is hypothetical reduced with the excess weight of 78 g (if it is allowed to cut that much off, otherwise with the maximum allowed) and the method is repeated starting with the first part of the method.

The best result from the two runs of the method is chosen as the result. The best result may be considered to be the one which provides the smallest excess weight.

Accordingly, in this embodiment, the determined weight of the food item $2a$ under consideration is processed together with a weight of a plurality of food items 2 in said food processing and the control cutting signal is dynamically generated to determine if cutting off a part of the food item $2a$ under consideration will increase a prospect to meet the at least one predefined batch target criterion. In this example, the predefined batch target criterion comprises at least one of the predefined item target weights (180 g and 135 g), which are compared as shown in the tables with the weights of the food item $2a$ under consideration together with a plurality of food items 2 in the list determining the accumulated excess weight. The accumulated excess weight is used to determine how the food item 2a under consideration should be processed.

If the result shows that the food item 2a under consideration advantageously can be reduced in size, then it may be checked if it is allowed to reduce the food item 2a under consideration in size. The check is performed to avoid that food items are unnecessarily reduced in weight.

Figure 2:
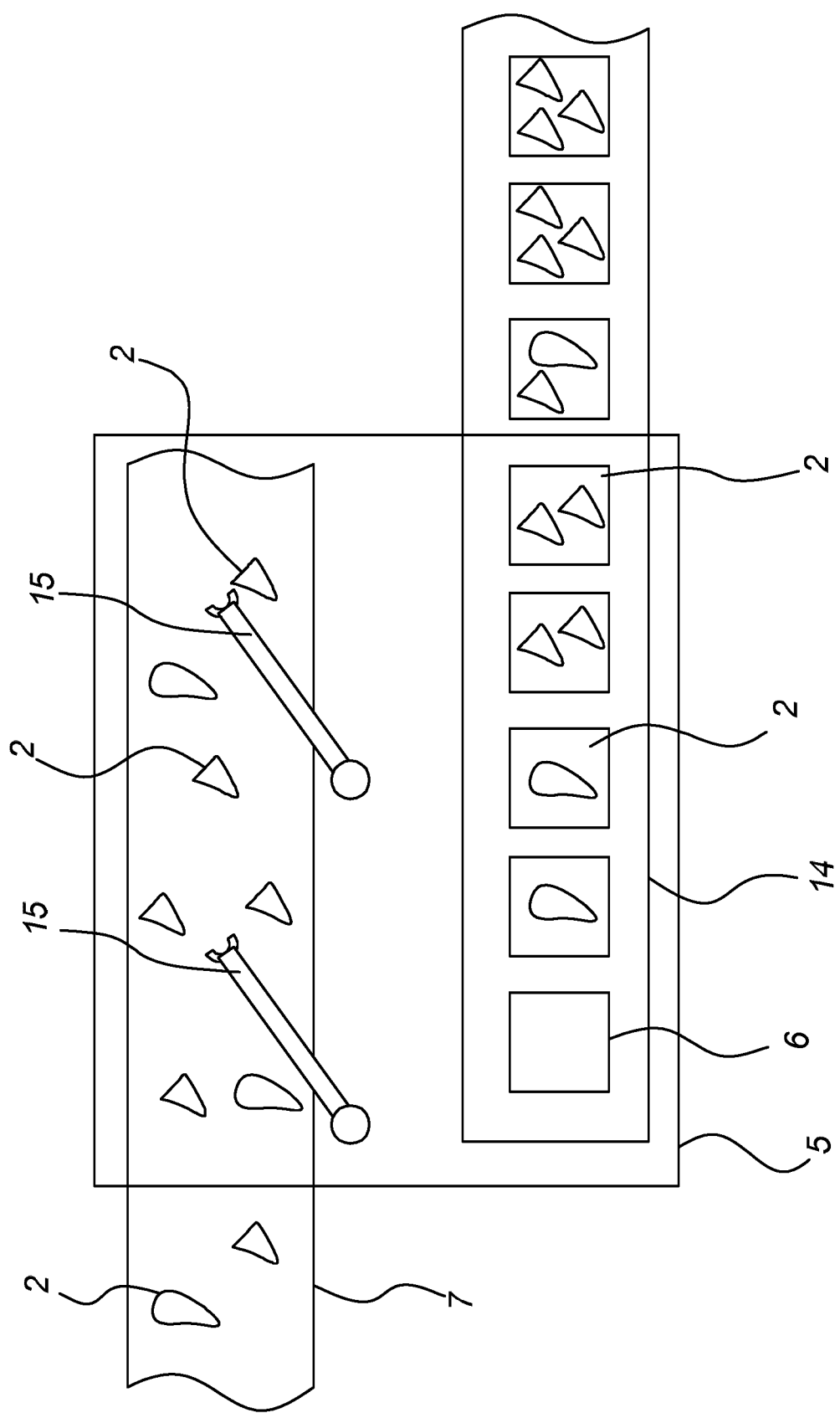
FIG. 2 shows the batching system of the food processing system.

FIG. 2 shows an embodiment of the batching system 5. The batching system 5 may comprise at least one controllable handling means 15, e.g. embodied by one or more robot arms, capable of transferring particular food items 2 from the conveyor means 7 to batches 6. The batches 6 may be of the same type or of different types, e.g. different types for accommodating different numbers of food items 2 and/or different total weights of food items in the batches. It is understood that different types of food item batches 6 may in fact be structurally identical, but intended for accommodating different numbers of food items. Batches 6 of the same type may also be used for accommodating different numbers of food items, where the batches are intended for accommodating the same or different batch weights. For example, batches 6 may be used for 400 g batch jobs, where each batch should contain two or three food items 2 with a total weight of at least 400 g .The batches 6 may be transported on a batch conveyor 14.

The batching system 5 may comprise a second vision station for determining the position of the food items entering the batching system. Accordingly, based on the determined position of the food items, the controllable handling means 15 can pick the individual food items 2 up and individually move them accurately to a position in a batch 6. The second vision station may be comprised by the batching system 5.

It is noted that the batching system 5 may be arranged to fill in food items 2 to a plurality of batches 6 gradually so that the batching system 5 may contain a number of unfinished batches 6, which are only partly filled, as illustrated in FIG. 2. The finally batched food items leave the batching system 5. In the example illustrated in FIG. 2, the batches of the finally batched food items contain two or three food items, some of which have been cut and some of which have not been cut.

In an embodiment the decision regarding which batch 6 the controllable handling means 15 should place the food item 2 in is based on the weight of at least the oldest one of the weight determined food items 2 that have not passed a certain decision point on the conveyor means 7 and the food items 2 that are already moved to unfinished batches 6. Several other methods on how to decide are known.

To reprise and sum-up adding some more:

According to an embodiment the food processing system 1 could operate as follows (reference is made to FIGS. 1 and 2):

The weight determining means 3 is in an embodiment of the invention identical with the shape determining means 9, e.g. a single vision station to determine or at least estimate both the volume and the shape of the food item 2.

The volume may be determined by means of a laser line illuminating the food item 2 e.g. from vertically above in a direction perpendicular to the conveyor direction and a camera to observe said laser line from an angle in the conveying direction or in the opposite direction of the conveying direction. When said laser line is observed in the described way it will appear as a non-straight line when an item is conveyed under it, where the diversion from straight is proportional to the height of the item. At the sides of the item the height is found to be zero, so in this way the width of the food item 2 is found. The length of the food item 2 is found by measuring the speed of the conveyor means 7 and use it in combination with the time the item influences the laser line detection.

In this way a volume versus length of the item can be formed and by means of a density factor, i.e. a weight to volume ratio, weights versus length curve. From this curve, it can be found where to cut off a desired portion (weight portion) of an item.

It is decided immediately after the volume and weight determination, for each food item 2, if the food item 2 has to be reduced in size (e.g. in weight), i.e. according to the examples for determining the control cutting signal and weight reduction described elsewhere.

Downstream to the volume determination, a food item separation device 4 is arranged. As previously described, in an embodiment, the food item separation device 4 comprises a sword-type knife that is suspended in a rotatable manner with its suspension point at the side of a gap in the conveyor means 7. Downstream to the food item separation device 4, optionally, a reject station 11 is positioned for automatically rejecting cut-off material of said food item, i.e. material which is not intended for batching. One way of performing the rejection is to open the conveyor means 7 such that the cut off part can fall through the opening. However, such an opening can be formed in several other ways e.g. as described in WO 2014 169925.

Downstream to the optional reject station 11, a further weight determining means 10 can be situated, i.e. downstream in relation to said separation device 4 and upstream in relation to said batching system 5. The further weight determining means 10 is arranged to determine the exact weight of the item (non-cut food item 2 or cut food item 13). The further weight determining means 10 will thereby (together with the control system 8) also check if the cut off part in fact has been rejected at the rejection station 11 (sometimes a cut off part sticks firmly together with the main piece and so it remains there). The further weight determining means 10 can furthermore be used to determine (or update) the density factor used to convert volume to weight (as explained above), because the weight of the non-size-reduced food items 2 (or possibly of all the food items 2 in the system 1) can be compared with the volume of the same food item 2, one by one. If the further weight determining means 10 is not present, the density factor has to be entered and maintained manually.

Downstream to the further weight determining means 10, a second vision station (not shown) can be situated. Here the exact position of the food item 2 can be determined such that the controllable handling means 15 can pick it up and move it accurately to a position in a batch 6. The second vision station may be comprised by the batching system 5.

The cut-off checking means 12 arranged for checking if cut-off material has been properly removed from the food item 2 may be situated downstream to the further weight determining means 10 and upstream relative to the batching system 5. As described elsewhere the cut-off checking means 12 can partly be identical to the further weight determining means 10.

Figure 3:
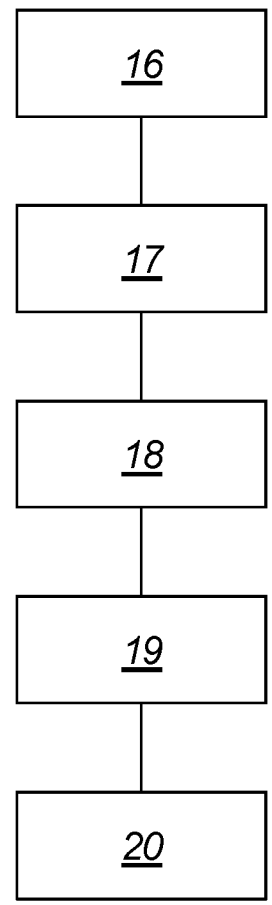
FIG. 3 shows steps of method of the invention.

FIG. 3 illustrates steps 16-20 of the method for processing and batching food items in a food processing system 1 (corresponding to steps 1-5 below), where said batching of food items 2, 2a is performed according to at least one predefined batch target criterion, said method comprises Step 1: conveying a food item 2a to weight determining means, Step 2: determining the weight of said food item 2a by means of said weight determining means 3, Step 3: processing said determined weight of said food item 2a together with a weight of a plurality of food items 2 in said food processing system, wherein the processing includes dynamically generating a control cutting signal, Step 4: if said dynamically generated control cutting signal indicates that cutting off a part of said food item 2a will increase a prospect to meet the at least one predefined batch target criterion, then convey said food item to a separation device wherein a part of said food item is cut off where after said food item is conveyed to a food item batching system, and Step 5: transporting said food item 2a to a food item batch 6 in response to said at least one predefined batch target criterion.

LIST

1. Food processing system
2. Food items
2a. Food item under consideration
3. Weight determining means
4. Separation device
5. Batching system
6. Food item batch
7. Conveyor means
8. Control system
9. Shape determining means
10. Additional weight determining means
11. Rejecter device
12. Cut-off checking means
13. Cut food item
14. Batch conveyor
15. Handling means
16. Method step 1
17. Method step 2
18. Method step 3
19. Method step 4
20. Method step 5

The invention claimed is:

1. A method for processing and batching food items in a food processing system, where said batching of food items is performed according to at least one predefined batch target criterion, said method comprising the steps of:
   conveying a food item to weight determining means,
   determining the weight of said food item by means of said weight determining means,
   processing said determined weight of said food item together with a weight of a plurality of food items in said food processing system, wherein the processing includes dynamically generating a control cutting signal,
   if said dynamically generated control cutting signal indicates that cutting off a part of said food item will increase a prospect to meet the at least one predefined batch target criterion, then convey said food item to a separation device wherein a part of said food item is cut off whereafter said food item is conveyed to a food item batching system, and
   transporting said food item to a food item batch in response to said at least one predefined batch target criterion;
   wherein said control cutting signal is only executed if the weight of said food item can be advantageously reduced by more than a predefined minimum cut-off weight.

2. The method according to claim 1, further comprising a step of determining if said dynamically generated control cutting signal indicates that cutting off a part of said food item will not increase said prospect to meet the at least one predefined batch target criterion, then convey said food item to said food item batching system without cutting off any part of said food item.

3. The method according to claim 1, further comprising a step of determining an average weight of a plurality of food items in said food processing system, and dynamically generating the control cutting signal and using the control cutting signal to reduce the weight of said food item, if reducing the weight of said food item will bring said average weight closer to an ideal average weight of said food item according to said at least one predefined batch target criterion.

4. The method according to claim 1, further comprising a step of comparing said determined weight of said food item with an average weight of a plurality of food items in said food processing system and dynamically generating the control cutting signal and using the control cutting signal to reduce the weight of said food item, if reducing the weight of said food item will bring said average weight closer to an ideal average weight of said food item according to said at least one predefined batch target criterion.

5. The method according to claim 1, wherein said plurality of food items includes at least some of the food items in food item batches in said food processing system.

6. The method according to claim 1, wherein said plurality of food items includes at least some of the food items having passed said separation device but have not already been batched.

7. The method according to claim 1, wherein said plurality of food items includes at least one food item having passed said weight determining means but have not passed said separation device.

8. The method according to claim 1, wherein said at least one predefined batch target criterion is at least one weight interval or at least one weight.

9. The method according to claim 1, comprising batching said food item in the food item batch in response to one or more predefined batching criteria.

10. The method according to claim 9, wherein said one or more predefined batching criteria comprise a number target regarding a number of food items in each food item batch.

11. The method according to claim 9, wherein said one or more predefined batching criteria comprise an appearance target regarding the appearances of the food items in each food item batch.

12. The method according to claim 9, wherein said one or more predefined batching criteria comprise two or more different weight targets.

13. The method according to claim 1, wherein said average weight is determined on the basis of the weight of at least four food items in said food processing system.

14. A food processing system for processing and batching food items, said food processing system comprising
   conveyor means for conveying said food items through at least parts of said food processing system,
   weight determining means for determining a weight of said food items,
   a batching system arranged to batch said food items according to one or more predefined batching criteria,
   a separation device positioned downstream in relation to the weight determining means and upstream in relation to the batching system, arranged to cut off a piece of said food items in accordance with a control cutting signal, and a control system for controlling the batching system and the separation device, wherein said control system is arranged for dynamically generating said control cutting signal on the basis of information regarding the determined weight of more than one food item in said food processing system;

wherein said control cutting signal is only executed if the weight of said food item can be advantageously reduced by more than a predefined minimum cut-off weight.

15. The food processing system according to claim 14, wherein said food processing system comprises a further weight determining means positioned downstream in relation to said separation device and upstream in relation to said batching system.

16. The food processing system according to claim 14, wherein said food processing system further comprises a rejecter device positioned downstream in relation to said separation device for automatically rejecting cut-off material of said food item.

17. The food processing system according to claim 14, wherein said basis of said information regarding the determined weight of said more than one food item includes at least one food item approaching said separation device and at least some of the food items having passed said separation device.

18. The food processing system according to claim 14, wherein said control system is arranged for using said information regarding said determined weight of said more than one food item to establish an average weight of said more than one food item and compare said determined weight of said food item with said average weight.

19. The food processing system according to claim 14, wherein said weight determining means further comprises shape determining means for determining a shape and a position of said food item.

20. The food processing system according to claim 19, wherein said separation device is adapted for cutting off said piece of said food item in response to input from said shape determining means.

21. The food processing system according to claim 14, wherein said food processing system comprises cut-off checking means arranged for checking if cut-off material has been properly removed from said food item.

22. The food processing system according to claim 21, wherein said control system is arranged to not batch a specific food item if said cut-off checking means detect that cut-off material has not been properly removed from said specific food item.

23. The method according to claim 1, further comprising the step of determining a total weight of the selection of food items minus the batch target weight multiplied by a number of items in the selection of food items divided by the number of items in each batch.

24. The method according to claim 1, further comprising the step of determining if a total weight of the selection of food items is greater than the predefined batch target weight multiplied by the number of food items in the selection of food items divided by the number of items in each batch.

* * * * *